(12) United States Patent
Curtis et al.

(10) Patent No.: US 6,344,042 B1
(45) Date of Patent: Feb. 5, 2002

(54) BONE AUGMENTATION DEVICE

(75) Inventors: Raymond Curtis, Davos Dorf (GB); Markus Hehli, Frauenkirch (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/709,733

(22) Filed: Nov. 13, 2000

Related U.S. Application Data

(63) Continuation of application No. PCT/EP98/02761, filed on May 12, 1998.

(51) Int. Cl.⁷ .................................. A61B 17/80
(52) U.S. Cl. ........................................ 606/69
(58) Field of Search ..................... 606/60, 61, 69, 606/70, 71, 232, 233

(56) References Cited

U.S. PATENT DOCUMENTS

| | | | |
|---|---|---|---|
| 3,533,410 A | 10/1970 | Shannon et al. | |
| 3,735,763 A | 5/1973 | Shannon et al. | |
| 5,306,301 A | 4/1994 | Graf et al. | 623/13 |
| 5,364,399 A | * 11/1994 | Lowery et al. | 606/69 |
| 5,766,175 A | * 6/1998 | Martinotti | 606/69 |

FOREIGN PATENT DOCUMENTS

| | | |
|---|---|---|
| DE | 32 11 682 | 10/1983 |
| EP | 0 520 177 A1 | 5/1992 |
| FR | 1550029 | 1/1968 |
| FR | 2422386 | 4/1978 |
| WO | 93/19678 | 4/1993 |
| WO | 9604852 A1 | 8/1995 |

* cited by examiner

Primary Examiner—David O. Reip
(74) Attorney, Agent, or Firm—Pennie & Edmonds LLP

(57) ABSTRACT

A bone augmentation device for attachment of soft tissue to bone by sutures includes a bone plate having top and bottom surfaces spaced equidistant from a central plane. At least one hole extends between the top and bottom surfaces and the holes preferably have rounded edges to minimize the potential to damage the suture. The central plane includes a longitudinal and a horizontal axis and the plate is curved along the longitudinal and horizontal axes to provide for a secure fit against the bone. The plate is made of a non-resorbable material.

17 Claims, 2 Drawing Sheets

BONE AUGMENTATION DEVICE

CROSS-REFERENCE TO RELATED APPLICATIONS

This application is a continuation of the U.S. National Stage designation of co-pending International Patent Application PCT/EP98/02761, filed May 12, 1998, the entire content of which is expressly incorporated herein by reference thereto.

FIELD OF THE INVENTION

The invention relates to a bone augmentation device. More particularly, the invention relates to a device for the attachment of soft tissues to bone by commonly used sutures.

BACKGROUND OF THE INVENTION

Attachment of soft tissue to bone is a technique frequently required in orthopaedic surgical procedures. Bone augmentation devices are often used in repair of soft tissue avulsions from bone as well as in reconstructive procedures and in particular for the attachment of avulsed tendons, ligaments, and joint capsules to bone. For example, bone augmentation devices may be used to help correct shoulder instability, rotator cuff tears, knee instability, tenodesis and ligamentous repair of the foot, ankle, and wrist.

One known procedure for soft tissue attachment to bone is the classic Bankart procedure which is a widely accepted method of treating anterior-inferior glen-humeral instability of the shoulder and uses sutures that are inserted directly through transosseous tunnels. Although this procedure leads to excellent clinical results, the procedure of reattaching the torn ligament or tendon can be time consuming and difficult. While modifications that decrease the operating time for standard rotator cuff and Bankart lesion repair are available, these approaches are technically demanding.

Another known method for soft tissue attachment to bone is the use of surgical staples, however, staples have a tendency to cut through the bone and tendon and may be unstable or cause gapping between the soft tissue and the bone which can lead to poor healing.

There exists a need for a device that is simple to administer and effects a stable attachment of soft tissue to bone to facilitate healing.

SUMMARY OF THE INVENTION

The present invention is related to a bone augmentation device for attachment of soft tissue to bone by sutures. The device comprises a bone plate having a central plane and top and bottom surfaces spaced equidistant from the central plane with at least one hole extending between the top and bottom surfaces. The central plane includes a longitudinal axis and a horizontal axis. The plate is curved along the longitudinal and horizontal axes with a radius of curvature between 25 to 100 mm. The plate is made of a non-resorbable implant material.

In one preferred embodiment, the plate has a radius of curvature between 35 to 70 mm, and in another embodiment the plate has a radius of curvature between 45 to 55 mm.

In the preferred embodiment, the plate defines hole edges at the intersection of the through holes with the top and bottom surfaces and the hole edges are rounded with a radius of curvature between 0.2 to 0.8 mm. In another embodiment, the radius of curvature of the hole edges can be between 0.25 to 0.50 mm. In yet another embodiment, the radius of curvature of the hole edges is between 0.3 to 0.4 mm.

The plate defines outer edges along the periphery of the top and bottom surfaces and the outer edges are rounded with a radius of curvature between 0.2 to 0.7 mm. In another embodiment, the radius of curvature of the outer edges is between 0.30 to 0.50 mm. In yet another embodiment, the radius of curvature of the outer edges is between 0.35 to 0.45 mm.

The plate has a thickness defined between the top and bottom surfaces and in the preferred embodiment the thickness is less than 1 mm. In another embodiment, the thickness is less than 0.75 mm.

In the preferred embodiment, the top and bottom surface have a surface area between 100 to 250 mm$^2$. In another embodiment, the top and bottom surface have a surface area between 125 to 175 mm.

In one embodiment, the plate has at least two through holes. In another embodiment, the plate has between 4 and 7 through holes.

In the preferred embodiment, the through holes have a diameter between 1.70 to 2.00 mm. In one embodiment, the through holes have a diameter between 1.80 to 1.90 mm. The through holes include a center and the distance between the centers in the preferred embodiment is between 3.0 to 4.3 mm. In other embodiments, the distance between the centers is between 3.4 to 3.8 mm.

In the preferred embodiment, the plate is made from titanium.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
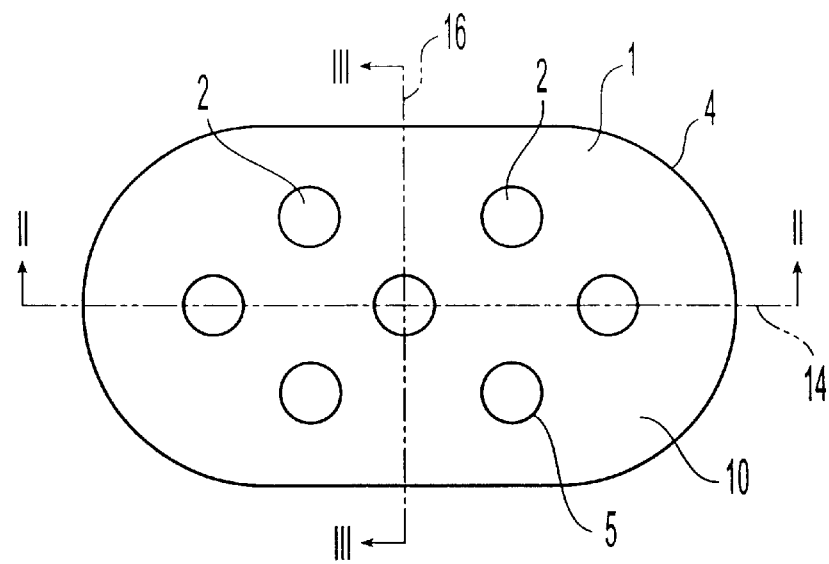
FIG. 1 is a top view of the device according to the invention.
Figure 2:
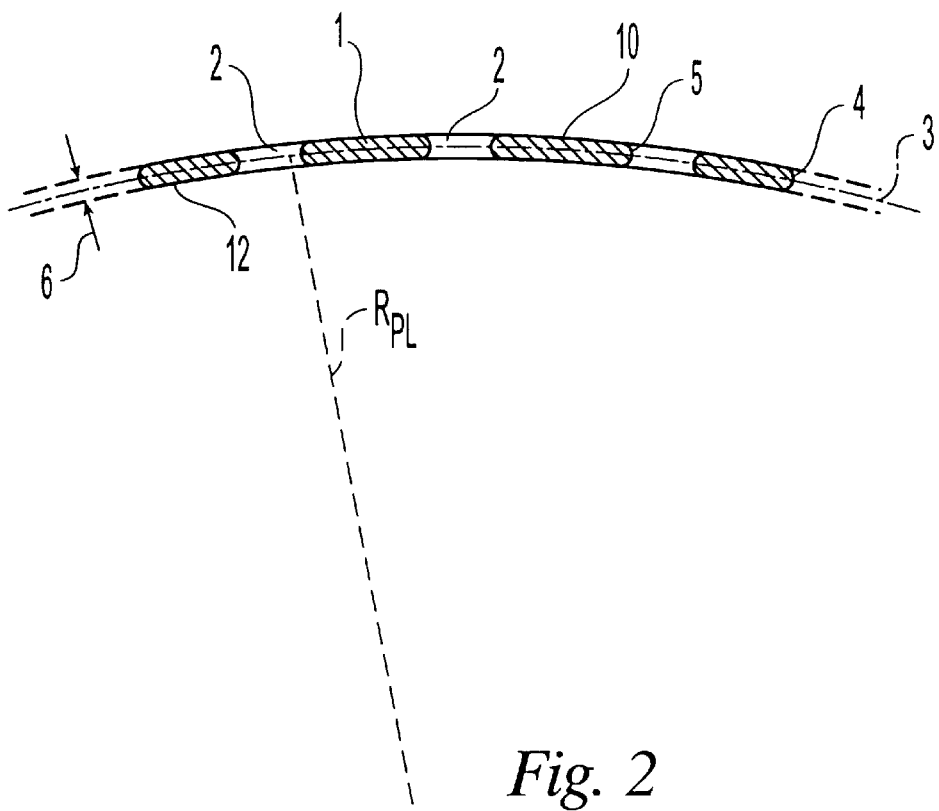
FIG. 2 is a cross-sectional view of the device taken along line II—II of FIG. 1.
Figure 3:
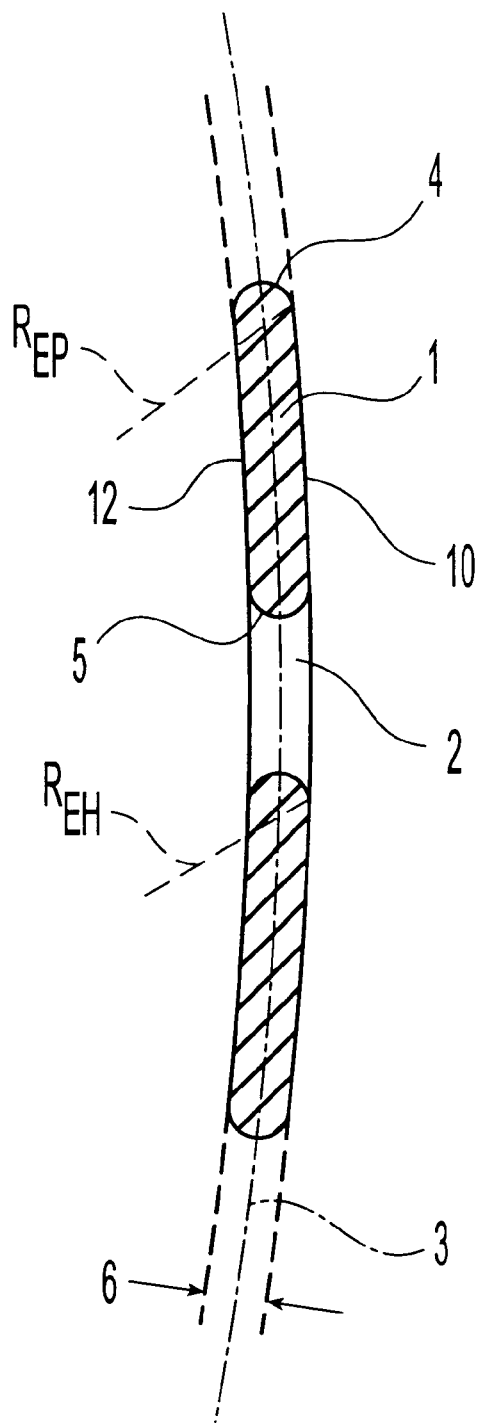
FIG. 3 is a cross-sectional view of the device taken along line III—III of FIG. 1.

Referring to FIGS. 1–3, a bone augmentation device is shown for attaching soft tissue to bone. The device includes a perforated curved plate 1 having a top surface 10 and a bottom surface 12 spaced equidistant from a central plane 3. In a preferred embodiment, top and bottom surfaces 10, 12 are generally oval shaped with a perimeter or outer edge 4. However, in alternate embodiments non-oval shapes may be used. Top and bottom surfaces 10, 12, and central plane 3 include a longitudinal or major axis 14 and a horizontal or minor axis 16.

Plate 1 includes a plurality of perforations or through holes 2 extending from top surface 10 to bottom surface 12, which are configured and dimensioned to receive a suture. Hole edges 5 are defined at the intersection of the through holes 2 with the top and bottom surfaces 10, 12. Plate 1 includes at least one, and preferably two through holes. In alternate embodiments between four and seven through holes may be provided. Holes 2 preferably have a diameter of about 1.85 mm and have centers preferably regularly spaced at about 3.6 mm from each other.

The plate is preferably curved to correspond to the shape of the bone which is advantageous to achieve a snug fit adjacent the bone when the plate is tightened there against with sutures. As can be seen in FIGS. 2 and 3, plate 1 and central plane 3 are curved along both the major and minor axes 14, 16. Preferably plate 1 and central plane 3 has a radius of curvature $R_{PL}$ between about 25 to 100 mm. In applications where the device is attached to the humerus, the radius of curvature $R_{PL}$ is between about 35 to 70 mm, preferably between about 45 to 55 mm. Most preferably the radius of curvature $R_{PL}$ is about 50 mm.

To prevent damage of a suture at sharp edges of the plate 1, preferably outer edges 4 and edges 5 of the through holes 2 are rounded. Outer edges 4 are preferably rounded with a radius of curvature $R_{EP}$ between about 0.2 to 0.7 mm, more preferably between about 0.25 to 0.50 mm, and most preferably about 0.35 mm. Edges 5 of the through holes 2 are preferably rounded with a radius of curvature $R_{EH}$ between about 0.2 to 0.8 mm, more preferably between about of 0.30 to 0.50 mm, and most preferably about 0.4 mm.

Top and bottom surfaces 10, 12 of plate 1 preferably have a surface area, including the area of the through holes 2, between about 100 to 250 mm$^2$, more preferably between about 125 to 175 mm$^2$, most preferably about 150 mm$^2$.

Plate 1 has a thickness 6, defined by the distance between top surface 10 and bottom surface 12. Preferably thickness 6 is below about 1 mm, more preferably below about 0.75 mm, and most preferably thickness 6 is about 0.7 mm.

In a preferred embodiment, plate 1 is made of a non-resorbable material such as titanium. Titanium advantageously can withstand relatively high loads and offers the possibility to design plates with a reduced thickness, as compared to some plastic materials. In alternate embodiments, other non-resorbable materials suitable for implantation in the human body may also be used.

When a bone augmentation device is utilized in a surgical procedure to attach a tendon to bone, first a tendon attachment site is selected by a surgeon. Using a burr or other excavating tool, a trough is created to receive a stump of maligned tendon. A hole or multiple holes are then created in the bone at the desired attachment site and suture stitches are created in the tendon. The end of the sutures are then passed through the holes in the bone and out the opposite end of the holes. The sutures are passed through the appropriate holes of the augmentation device and the augmentation device is placed adjacent the bone and overlying the holes. The sutures are then tightened such as by tying knots and as the sutures are tightened the avulsed tendon and augmentation device are pulled tightly onto the bone. As a result, the augmentation device is held firmly adjacent the bone and the device prevents the sutures from cutting through the bone and the repair is advantageously stable. The rounded hole edges and perimeter edges of the device prevent the sutures from being frayed or cut and also facilitates stability of the repair. Also, the soft tissue (tendon) is held tightly onto the bone and prevents gapping between the end of the tendon and bone which could result in poor healing.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A bone augmentation device for attachment of soft tissue to bone by sutures, comprising:

a bone plate having a central plane and top and bottom surfaces spaced equidistant from the central plane and defining at least one through hole extending between the top and bottom surfaces, the central plane including a longitudinal axis and a horizontal axis, wherein the plate is preformed to conform to bone and is curved along the longitudinal and horizontal axes and has a radius of curvature between about 25 and 100 mm, and the plate is made of a non-resorbable material.

2. The device of claim 1, wherein the plate has a radius of curvature between about 35 and 70 mm.

3. The device of claim 2, wherein the plate has a radius of curvature between about 45 and 55 mm.

4. The device of claim 1, wherein the plate defines hole edges at the intersection of the at least one through hole with the top and bottom surfaces and the hole edges are rounded with a radius of curvature between about 0.2 and 0.8 mm.

5. The device of claim 4, wherein the radius of curvature of the hole edges is between about 0.25 and 0.50 mm.

6. The device of claim 1, wherein the plate defines outer edges along the periphery of the top and bottom surfaces and the outer edges are rounded with a radius of curvature between about 0.2 and 0.7 mm.

7. The device of claim 6, wherein the radius of curvature of the outer edges is between about 0.30 and 0.50 mm.

8. The device of claim 1, wherein the plate has a thickness defined between the top and bottom surfaces and the thickness is less than 1 mm.

9. The device of claim 1, wherein the thickness is less than 0.75 mm.

10. The device of claim 8, wherein the top and bottom surface have a surface area between about 100 and 250 mm$^2$.

11. The device of claim 10, wherein the top and bottom surface have a surface area between about 125 and 175 mm$^2$.

12. The device of claim 1, wherein the plate has at least two through holes.

13. The device of claim 12, wherein the plate has between 4 and 7 through holes.

14. The device of claim 12, wherein the through holes include a center and the distance between the centers is between about 3.0 and 4.3 mm.

15. The device of claim 1, wherein the at least one through hole has a diameter between about 1.70 and 2.00 mm.

16. The device of claim 1, wherein the at least one through hole has a diameter between about 1.80 and 1.90 mm.

17. The device of claim 1, wherein the plate is made from titanium.

* * * * *